United States Patent [19]

Muckenfuhs et al.

[11] Patent Number: 4,934,535
[45] Date of Patent: Jun. 19, 1990

[54] EASY OPEN FLEXIBLE BAG FILLED WITH COMPRESSED FLEXIBLE ARTICLES AND METHOD AND APPARATUS FOR MAKING SAME

[75] Inventors: Delmar R. Muckenfuhs, Middletown; James C. Baird, Cincinatti, both of Ohio

[73] Assignee: The Procter & Gamble Company, Cincinnati, Ohio

[21] Appl. No.: 333,204

[22] Filed: Apr. 4, 1989

[51] Int. Cl.⁵ ............................................. B65D 77/32
[52] U.S. Cl. .................... 206/610; 206/628; 383/8; 383/10; 221/63; 221/302
[58] Field of Search ............... 206/610, 628, 620, 634; 383/8, 10, 120; 221/63, 302

[56] References Cited

U.S. PATENT DOCUMENTS

| | | | |
|---|---|---|---|
| D. 135,538 | 4/1943 | Kaplan . | |
| 655,998 | 8/1900 | Taylor . | |
| 1,261,612 | 4/1918 | Powers . | |
| 1,733,219 | 10/1929 | Duvall . | |
| 1,920,841 | 8/1933 | Clark . | |
| 2,011,236 | 8/1935 | Winter et al. . | |
| 2,127,118 | 8/1938 | Herbelin . | |
| 2,196,185 | 4/1940 | Belcher . | |
| 2,506,021 | 5/1950 | Holmberg . | |
| 2,700,459 | 1/1955 | Anspacher . | |
| 2,781,161 | 2/1957 | Adams . | |
| 2,998,911 | 9/1961 | Hahn et al. | 206/610 |
| 3,006,119 | 10/1961 | Fingerhut . | |
| 3,044,228 | 7/1962 | Peterson . | |
| 3,056,245 | 10/1962 | Baum et al. . | |
| 3,059,387 | 10/1962 | Fasanella . | |
| 3,117,513 | 1/1964 | Burnett et al. . | |
| 3,124,298 | 3/1964 | Repko | 206/610 |
| 3,161,336 | 12/1964 | Loescher . | |
| 3,173,188 | 3/1965 | Wexler . | |
| 3,206,105 | 9/1965 | Smith . | |
| 3,327,449 | 6/1967 | Hullhorst et al. . | |
| 3,361,041 | 1/1968 | Grob . | |
| 3,370,630 | 2/1968 | Haugh et al. . | |
| 3,381,440 | 5/1968 | Hullhorst . | |
| 3,514,033 | 5/1970 | Goodwin . | |
| 3,548,723 | 12/1970 | Sengewald . | |
| 3,593,622 | 7/1971 | Sengewald . | |

(List continued on next page.)

FOREIGN PATENT DOCUMENTS

3102192  9/1982  Fed. Rep. of Germany ........ 383/10

Primary Examiner—Stephen Marcus
Assistant Examiner—K. M. Stemann
Attorney, Agent, or Firm—E. Kelly Linman; John V. Gorman; Richard C. Witte

[57] ABSTRACT

An easy open flexible bag containing one or more stacks of flexible articles maintained in a state of compression in a direction substantially parallel to their thickness. For products such as disposable absorbent baby diapers, catamenial pads, incontinent briefs and the like, the degree of compression within the bag may be as much as 50% or more when compared to the uncompressed thickness of the stack of articles in question. In a particularly preferred embodiment, the bag totally encloses the stack or stacks of compressed flexible articles exhibits a substantially rectilinear shape. The bag preferably includes an integral carrying handle. The end panels and at least one pair of either the front and back or the top and bottom panels of the bag are subject to tension imposed by the stack of compressed flexible articles. This leaves at least one pair of panels, preferably the top and bottom panels, in a substantially untensioned condition. One of the substantially untensioned top and bottom panels contains an easily visible, unobstructed tear initiating device which comprises a portion of the easy open device for the bag. The tear initiating device can be readily activated by the end user's fingers to create an aperture traversing at least one corner of the bag. Partially pre-erected easy open flexible bags of the present invention are filled by over-compressing the flexible articles to a dimension which is smaller than the interior of the bag and thereafter allowing the articles to expand slightly once they have been inserted within the bag. Preferred apparatus for compressing the flexible articles and inserting them into partially pre-erected flexible bags of the present invention are also disclosed.

12 Claims, 8 Drawing Sheets

U.S. PATENT DOCUMENTS

| | | | |
|---|---|---|---|
| 3,605,570 | 9/1971 | Goodwin . | |
| 3,729,886 | 5/1973 | Lucas et al. . | |
| 3,818,673 | 6/1974 | Rollins et al. . | |
| 3,824,759 | 7/1974 | Finn et al. . | |
| 3,977,596 | 8/1976 | Gamble | 383/10 |
| 4,031,815 | 6/1977 | Verbeke . | |
| 4,047,362 | 9/1977 | Lister et al. . | |
| 4,062,169 | 12/1977 | Lister et al. . | |
| 4,074,508 | 2/1978 | Reid . | |
| 4,182,237 | 1/1980 | O'Brien . | |
| 4,216,899 | 8/1980 | Kamp . | |
| 4,241,562 | 12/1980 | Meyer . | |
| 4,252,269 | 2/1981 | Peppiatt . | |
| 4,328,655 | 5/1982 | Spencer et al. . | |
| 4,414,788 | 11/1983 | Berg . | |
| 4,501,107 | 2/1985 | Piotrowski . | |
| 4,539,705 | 9/1985 | Baines | 383/8 |
| 4,550,439 | 10/1985 | Peppiatt et al. | 383/8 |
| 4,573,203 | 2/1986 | Peppiatt | 383/8 |
| 4,577,453 | 3/1986 | Hofeler | 53/438 |
| 4,602,472 | 7/1986 | Ampolini et al. | 53/438 |
| 4,604,084 | 8/1986 | Pistner | 493/226 |
| 4,605,392 | 8/1986 | Achelpohl et al. | 493/196 |
| 4,607,388 | 8/1986 | Koiyumaki et al. | 383/121 |
| 4,608,808 | 9/1986 | Ryan et al. | 53/436 |
| 4,609,366 | 9/1986 | Ley et al. | 493/22 |
| 4,610,029 | 9/1986 | Huhtala et al. | 383/10 |
| 4,613,988 | 9/1986 | Maddock | 383/8 |
| 4,628,535 | 12/1986 | Tetenborg | 383/24 |
| 4,632,244 | 12/1986 | Landau | 206/219 |
| 4,633,649 | 1/1987 | Gautier et al. | 53/413 |
| 4,636,191 | 1/1987 | Piggott | 493/227 |
| 4,638,913 | 1/1987 | Howe, Jr. | 206/632 |
| 4,660,352 | 4/1987 | Deines et al. | 53/438 |
| 4,660,354 | 4/1987 | Lancaster et al. | 53/469 |
| 4,661,989 | 4/1987 | Risby | 383/2 |
| 4,664,957 | 5/1987 | van de Pol | 428/35 |
| 4,677,810 | 7/1987 | Spano | 53/428 |
| 4,685,276 | 8/1987 | Kiel | 53/459 |
| 4,686,815 | 8/1987 | Zils et al. | 53/469 |
| 4,688,369 | 8/1987 | Cornish et al. | 53/436 |
| 4,688,370 | 8/1987 | Dighton et al. | 53/469 |
| 4,688,372 | 8/1987 | Langen et al. | 53/529 |
| 4,691,368 | 9/1987 | Roessinger | 383/10 |
| 4,691,369 | 9/1987 | Costa | 383/17 |
| 4,694,638 | 9/1987 | Maddux, Jr. et al. | 53/459 |
| 4,696,050 | 9/1987 | Sengewald | 383/10 |
| 4,696,145 | 9/1987 | Schmidt et al. | 53/436 |
| 4,699,608 | 10/1987 | Pistner | 493/204 |
| 4,702,731 | 10/1987 | Lambrecht et al. | 493/196 |
| 4,703,517 | 10/1987 | Marino | 383/7 |
| 4,704,100 | 11/1987 | Kaufman | 493/194 |
| 4,706,440 | 11/1987 | Bittner | 53/438 |
| 4,710,967 | 12/1987 | Petschner | 383/8 |
| 4,711,066 | 12/1987 | Fox et al. | 53/436 |
| 4,713,135 | 12/1987 | Bridgeford | 156/218 |
| 4,713,839 | 12/1987 | Peppiatt | 383/29 |
| 4,715,635 | 12/1987 | Koskinen | 294/68.1 |
| 4,717,262 | 1/1988 | Roen et al. | 383/120 |
| 4,720,872 | 1/1988 | Kaczerwaski | 383/8 |
| 4,721,396 | 1/1988 | Sengewald | 383/8 |
| 4,730,942 | 3/1988 | Fulcher | 383/7 |
| 4,730,943 | 3/1988 | Johnson | 383/8 |
| 4,738,546 | 6/1988 | Sengewald | 383/120 |

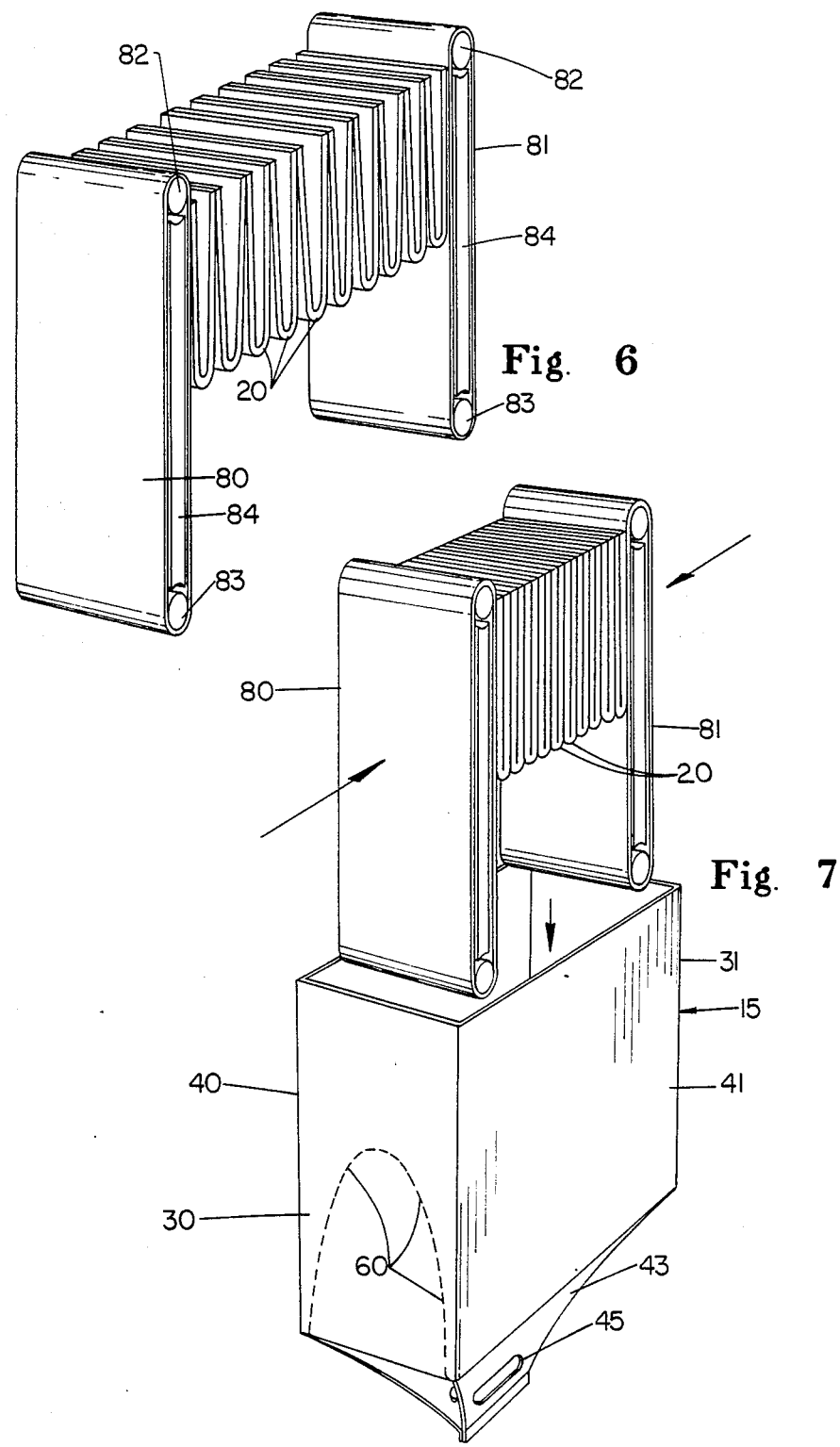

EASY OPEN FLEXIBLE BAG FILLED WITH COMPRESSED FLEXIBLE ARTICLES AND METHOD AND APPARATUS FOR MAKING SAME

TECHNICAL FIELD

The present invention relates to an easy open flexible bag filled with compressed flexible articles.

The present invention further relates to such an easy open bag wherein the flexible articles are compressed to as much as 50% or more of their initial thickness.

The present invention further relates to such an easy open flexible bag containing a stack of compressed articles which, upon activation of the easy open feature, begin to partially expand from the inner confines of the bag to produce a fan-like array of articles to permit easy one-at-a-time removal of the articles from the bag.

The present invention further relates to such an easy open flexible bag wherein the compressed articles tend to automatically feed into the aperture formed in the bag by activation of the easy open feature, at least until such time as the articles remaining within the bag return to their initially uncompressed thickness.

The present invention further relates to such an easy open flexible bag which can be constructed of relatively low cost flexible materials such as polymeric films, papers, nonwovens, or laminate structures comprised of two or more of such low cost materials.

The present invention has further relation to method and apparatus for making such easy open flexible bags of compressed flexible articles.

The present invention further relates to the use of such easy open flexible bags to reduce the volume normally occupied by flexible articles such as disposable diapers, catamenial pads, incontinent briefs, and the like, thereby reducing the storage, transportation and handling costs normally incurred when such articles are distributed in a substantially uncompressed condition. Importantly, these benefits inhere not only for the manufacturer, but also for the retailer and the end user.

Finally, the present invention relates to the use of easy open flexible bags of the present invention to optimize pallet fit during handling, storage and transport operations, i.e., the amount of compression applied to the flexible articles is preferably selected so that the overall dimension for an integral number of bags substantially coincides with the corresponding overall dimension of the pallet on which the filled bags are stacked.

BACKGROUND ART

Relatively soft and flexible compressible articles such as disposable diapers, catamenial pads, incontinent briefs and the like have entered widespread use in many parts of the world over the last 20–30 years. Many of these products are produced as continuous webs which are typically folded one or more times parallel to the direction of web travel as they travel through the converting lines in the machine direction and are ultimately cut from the web to form discrete single use articles. The discrete articles are typically folded at their midpoint, collected in stacks and inserted into paperboard or cardboard cartons or flexible bags while they are subject to little or no compression in a direction substantially parallel to their thickness.

In such circumstance, the dimensions of the paperboard or cardboard carton or flexible bag are generally determined by the number of discrete articles contained in the stack or stacks placed within the carton or bag.

Recent consumer purchasing trends in the disposable absorbent products field, particularly in the United States, have led to lower purchase frequencies with larger quantities of disposable absorbent products per purchase. Manufacturers have responded by continuing to increase the number of discrete articles contained within a single package, resulting in a number of jumbo packs containing relatively large quantities of disposable absorbent products such as baby diapers, e.g., 32, 48, 64, 96, etc. Because of the bulk of the relatively low density flexible compressible articles in question, this has resulted in packages having high volume but low weight. This combination of high volume and low weight increases storage and handling costs for the manufacturer, rapidly exhausts the limited shelf space of the retailer, and detracts from the convenience of storage and use for the consumer.

In addition, the relatively large volume of package material required to house the disposable absorbent articles in an uncompressed condition must be disposed of when the package in question has been fully emptied. In the case of cartons, this requires further effort by the end user to crush or otherwise minimize the volume of the empty container before placing it in the trash.

OBJECTS OF THE INVENTION

Accordingly, it is an object of the present invention to overcome or at least reduce the severity of the aforementioned storage, handling and disposability problems associated with prior art packages of substantially uncompressed flexible articles, while simultaneously providing improved convenience for and acceptance by the end user.

It is another object of the present invention to provide an easy open flexible package of compressed flexible articles which can simultaneously overcome many of the problems of the prior art packages of substantially uncompressed articles, as described in the preceding paragraphs, while simultaneously reducing the costs incurred by the manufacturer.

It is another object of the present invention to provide an easy open flexible bag filled with compressed flexible articles which can be comprised of relatively inexpensive materials such as polymeric films, papers, nonwovens, or a laminate comprising two or more of such materials, thereby decreasing the severity of the disposal problem from an environmental standpoint both with respect to the amount of packaging material required and the disposability/degradability of the particular bag material selected.

It is still another object of the present invention to provide an easy open flexible bag of compressed flexible articles which exhibits an unobstructed opening feature which can readily be found by the end user and which can be easily and reliably opened by gripping with the user's fingers and tearing along a predetermined line of weakness in the bag material.

It is still another object of the present invention to provide such an easy open flexible bag filled with compressed flexible articles which, upon activation of the easy open feature, will cause the unrestrained portion of the compressed articles housed within the bag to partially project in a fan-like arrangement through the aperture created in the tensioned end panel of the bag. This permits easy one-at-a-time removal of discrete articles from the bag, at least until such time as the compressive forces acting upon the articles remaining in the bag have been substantially relieved.

DISCLOSURE OF THE INVENTION

The present invention, in a particularly preferred embodiment, comprises an easy open flexible bag containing one or more stacks of flexible articles maintained in a state of compression in a direction substantially parallel to their thickness. For products such as disposable absorbent baby diapers, catamenial pads, incontinent briefs and the like, the degree of compression within the bag may be as much as 50% or more when compared to the uncompressed thickness of the stack of articles in question.

In a particularly preferred embodiment, the bag totally encloses the stack or stacks of compressed flexible articles and exhibits a substantially rectilinear shape. The flexible bag preferably comprises a front panel and a back panel connected to one another by means of a pair of end panels. A bottom panel and a top panel are preferably secured about their peripheries to the lowermost and uppermost edges of the front and back panels and the end panels. A stack of compressed articles oriented so that their substantially planar surfaces are aligned substantially parallel to the end panels of the bag while the exposed peripheral edges of the articles contained within the stack are aligned substantially parallel to the front, back, bottom and top panels of the bag and are preferably totally enclosed within the bag. The entire exposed substantially planar surface of each outermost article in the stack intimately contacts the innermost surface of the adjacent end panel, while only the outermost peripheral edges of the articles contained within the stack contact the front, back, top and bottom panels of the bag. The end panels and at least one pair of either the front and back or the top and bottom panels are subject to tension imposed by the stack of compressed flexible articles. As will be explained in greater detail hereinafter, this leaves at least one pair of panels in a substantially untensioned condition. One of the substantially untensioned top and bottom or front and back panels contains an easily visible, unobstructed tear initiating device which comprises a portion of the easy open device for the bag. The tear initiating device can be readily activated by the end user's fingers to create an aperture traversing at least one corner of the bag.

The easy opening device employed in a particularly preferred embodiment of the present invention comprises a substantially continuous line of weakness traversing a portion of one of the end panels of the bag and extending into the adjacent substantially untensioned front, back, bottom or top panel. The line of weakness can be formed by many means well known in the art including, for example only, perforations in the bag material. The portion of the line of weakness contained within the end panel in question exhibits a shape approximating up to about 75% of the cross-sectional shape of the stack of articles contained in the package. The portion of the line of weakness extending into the adjacent untensioned front, back, bottom or top panel preferably converges from a width which is only slightly less than the width of the end panel to form a generally tapered outline leading to a tear initiating point which can be easily grasped between the user's thumb and forefinger. If desired, the tear initiating point for initiating removal of the bag material defined by the continuous line of weakness can be fully cut and/or reinforced to facilitate grasping. In addition, graphical indicia may be provided on the bag to highlight the location of the tear initiating point in one of the substantially untensioned panels of the bag.

In a particularly preferred embodiment, the easy open flexible bag of compressed flexible articles is provided with extensions of the front and back walls of the package, said extensions being secured to one another above the panel containing the tear initiating point. The user's arm can be inserted through the loop thus formed to facilitate carrying the bag. Alternatively, each extension may contain an aperture for insertion of the user's fingers to facilitate carrying of the bag with the user's hand. In either case, the extensions of the front and back panels are preferably tapered to form a handle which is much smaller in overall length than the length of the bag. To facilitate easy location of the tear initiating point in the subjacent substantially untensioned top panel, the tear initiating point is preferably located directly beneath the point at which the front and back panel extensions are secured to one another, as viewed from directly overhead. Thus, the end user's fingers are automatically guided to the tear initiating point by the exposed tapered edges of the front and back panel extensions which converge to the point where the panel extensions are secured to one another. If desired, graphical indicia can be further added to the front and back panel extensions or to other portions of the bag to direct the user's attention to the tear initiating point.

By placing the tear initiating point in that portion of the continuous line of weakness which lies in a substantially untensioned panel, the portion of the line of weakness in the substantially untensioned panel may be designed for easy rupture without risking premature opening of the bag during shipping and handling. Conversely, that portion of the continuous line of weakness contained within the tensioned end panel preferably employs a line of weakness which requires a higher level of force to propagate the tear. This minimizes the chance that tensile forces exerted by the compressed flexible articles will cause premature opening of the bag before it reaches the end user.

Easy open flexible bags of compressed flexible articles of the present invention are opened by grasping the unobstructed tear initiating point in the portion of the line of weakness contained within one of the substantially untensioned panels and stripping the material defined by the line of weakness from the substantially untensioned panel and the adjacent tensioned end panel until an aperture bridging the substantially untensioned panel and extending to as much as about 75% of the depth of the tensioned end panel has been formed. The bag material defined by the line of weakness may be completely removed from the bag or left pivotally connected thereto at its lowermost edge, as desired by the end user.

Because the stack of articles contained within easy open flexible bags of the present invention is maintained in compression by the bag, removal of one corner of the bag in the aforementioned manner permits the unrestrained portion of the stack of articles to expand in a fan-like array through the aperture in the bag while the portion of the stack coinciding with the remaining tensioned portion of the end panel is retained in a substantially compressed condition. This facilitates easy grasping and removal of discrete articles from the stack one-at-a-time. Expansion of the unrestrained portion of the stack in the aforementioned manner will continue, at least until such time as the articles remaining within the bag have returned to their substantially uncompressed thickness. Thus, the end user is provided with a convenient, automatically assisted dispensing feature which functions throughout a substantial portion of the bag's useful life. The last few articles remaining in the bag may also be easily removed from the bag due to the easy access provided by removal of an entire corner of the bag.

While techniques are generally known for producing heat shrinkable film bags wherein the articles contained within are subjected to a degree of compression, the levels of article compression which can be achieved utilizing such techniques are generally quite limited due to the limited shrinking forces imposed on the articles when such films are heated. By way of contrast, partially pre-erected easy open flexible bags of the present invention are filled by over-compressing the flexible articles to a dimension which is smaller than the interior of the bag and thereafter allowing the articles to expand slightly once they have been inserted within the bag. Thus, finished easy open bags of the present invention exhibiting levels of compression as much as 50% or more relative to the uncompressed height of the stack of articles in question can readily be achieved by selecting bag materials exhibiting sufficient tensile strength.

Preferred apparatus for compressing the flexible articles and inserting them into partially pre-erected flexible bags of the present invention comprise a pair of opposing knife belts which will be described in greater detail hereinafter.

BRIEF DESCRIPTION OF THE DRAWINGS

While the specification concludes with claims particularly pointing out and distinctly claiming the present invention, it is believed the present invention will be better understood from the foregoing description in conjunction with the accompanying drawings in which:

FIG. 6 is a simplified schematic illustration of a pair of knife belt assemblies which are preferably employed to compress a stack of flexible articles to be housed within an easy open flexible bag of the present invention, said view being taken prior to compression of the stack of flexible articles;

FIG. 7 is a simplified perspective view of the apparatus of FIG. 7 shown after the stack of flexible articles has been compressed, but prior to inserting of the knife belt assemblies and the stack of compressed articles into the bottom of a partially pre-erected easy open flexible bag of the present invention;

DETAILED DESCRIPTION OF THE INVENTION

While the present invention will be described in the context of providing an easy open flexible bag containing one or more stacks of folded disposable absorbent diapers, the present invention is in no way limited to such application. The present invention may in fact be practiced to great advantage to provide reduced storage, shipping and handling costs in any situation involving flexible articles which are substantially compressible in at least one of their dimensions, such as their thickness. In addition, the present invention can be practiced to great advantage to provide automatically assisted dispensing of discrete flexible articles one-at-a-time due to the action of the compressive forces acting upon the flexible articles during a substantial portion of the bag's useful life. The detailed description contained herein, which relates to a particularly preferred easy open flexible bag of compressed disposable diapers, will allow one skilled in the art to readily adapt the invention to other uses.

Figure 1:
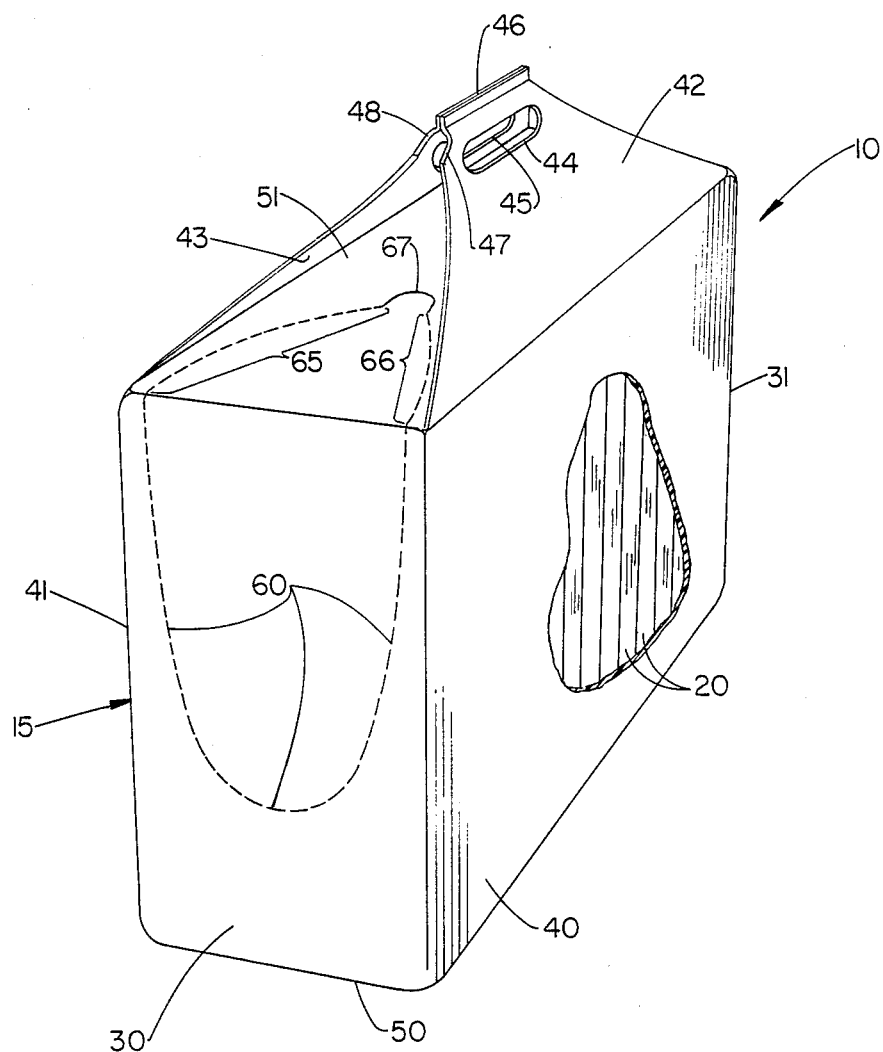
FIG. 1 is a simplified perspective view of a particularly preferred easy open flexible bag of compressed flexible articles of the present invention, said view including a broken away segment to more clearly show the content of the bag.

FIG. 1 is a simplified perspective illustration of a particularly preferred embodiment 10 of an easy open flexible bag of compressed flexible articles 20 of the present invention. The compressed articles 20 may comprise disposable absorbent diapers such as those disclosed in commonly assigned U.S. Pat. No. 3,860,003 issued to Buell on Jan. 14, 1975 and hereby incorporated herein by reference. Prior to stacking and insertion into the bag, the diapers 20 are typically folded one or more times in a direction generally parallel to the machine direction during converting so that the ears of each hourglass shaped diaper overlie the central portion of the diaper. The diapers 20 are also preferably folded about their midpoints after being cut from a continuous web and prior to being collected into stacks. The resultant cross-section of the stack of diapers 20 is substantially rectangular and substantially coincides with the shape of end panels 30 and 31 of the flexible bag 15.

Prior to insertion into the bag 15, the stack of folded disposable diapers 20 is subjected to compression to reduce the overall dimension of the stack by as much as 50% or more relative to the uncompressed height of the stack.

It has been learned that relatively high levels of compression of disposable absorbent articles can be performed without introducing any appreciable lasting negative effects to the individual articles, provided the articles are not caused to undergo yielding during the compression step. Experience has demonstrated that the risk of causing yielding is minimal if the compression step is carried out while the articles are in stacks. Accordingly, diapers compressed while in a stack and thereafter retained under a degree of compression in easy open flexible bags of the present invention typically reach the end user without suffering any lasting negative effects as a result of the compression.

As can be seen from FIG. 1, the stack of compressed diapers 20 is maintained in its compressed state by opposing end panels 30 and 31 of flexible bag 15. End panels 30 and 31 are joined to front wall 40, back wall 41, bottom wall 50 and top wall 51, as generally shown in FIG. 1. In order to maintain the stack of disposable diapers 20 in a compressed condition, either the front and back panels 40 and 41 or the bottom and top panels 50 and 51 must be subject to tension.

In the illustrated embodiment of FIG. 1, the tension required to keep the disposable absorbent diapers 20 in a compressed state is carried by end panels 30 and 31 and front panel 40 and back panel 41. Bottom panel 50 and top panel 51 are in a substantially untensioned condition.

The easy open feature of bag 15 comprises a substantially continuous line of weakness which traverses end panel 30 and one of the substantially untensioned panels, in the illustrated case, top panel 51. The substantially continuous line of weakness comprises a portion 60 in end panel 30 which may be comprised of perforations. The balance of the line of weakness comprises portions 65, 66 and 67 which traverse substantially untensioned top panel 51, as generally shown in FIG. 1. Portions 65 and 66 of the line of weakness may also be comprised of perforations which preferably converge in triangular fashion near the central portion of the substantially untensioned top panel 51 at a tear initiating point 67 which may be fully cut through the bag material, as generally shown in FIG. 1.

Because portions 65, 66 and 67 of the continuous line of weakness are located in a substantially untensioned panel, this portion of the line of weakness may be designed to rupture at relatively low levels of applied force. Conversely, because end panel 30 is subject to tension, the perforations or other form of weakening employed to create the line of weakness are preferably more resistant to tearing. This minimizes the chance of premature opening of the bag due to the tensile forces imposed by the compressed articles 20 contained within the bag.

In the particularly preferred embodiment 10 of the present invention illustrated in FIG. 1, the front panel 40 of the bag is provided with a vertical extension 42 and the back panel 41 of the bag is provided with a vertical extension 43 which are joined to one another by means of a heat seal, adhesive, etc. at a point 46 located above the substantially untensioned top panel 51 of the bag. The front panel extension 42 and the back panel extension 43 are preferably tapered so as not to obscure either visibility or access to the portion of the line of weakness contained in the subjacent substantially untensioned top panel 51. The end user may carry the bag by inserting his or her arm through the loop formed by the panel extensions. Alternatively, a pair of finger grip apertures 44,45 may be provided in the front panel extension 42 and back panel extension 43, respectively, as generally shown in FIG. 1, to facilitate easy carrying of the preferred easy open flexible bag of compressed flexible articles 10 with the user's hand. In a particularly preferred embodiment, the exposed tapered edges of the front panel extension 42 and back panel extension 43 have a shape which, when viewed from directly overhead, substantially coincides with that portion of the line of weakness contained in the underlying substantially untensioned top panel 51. In this regard note particularly circular indentations 47 and 48 in front panel extension 42 and back panel extension 43, respectively, which have a shape substantially corresponding to that of the tear initiating point 67 in the underlying substantially untensioned top panel 51.

With the latter arrangement, the user's fingers are guided to the tear initiating point 67 by merely running the fingers along the exposed tapered edge of front panel extension 42 or back panel extension 43 to the point 46 where the front and back panel extensions are joined to one another. If desired, colorful graphical indicia can be added to the exterior of the front and/or back panel extensions 42 and 43 or to other portions of the bag, as deemed appropriate, to highlight the location of the tear initiating point 67.

As will be appreciated from the foregoing description, the use of vertical panel extensions to provide carrying handles for the bag is a highly desirable optional method of providing both carrying convenience and assisting the end user to easily locate the tear initiating point to initiate the bag opening and dispensing cycle. It will be appreciated that the easy open flexible bag of compressed flexible articles 10 shown in FIG. 1 contemplates that substantially untensioned panel 50 will act as the bottom of the bag in use and that the compressed disposable diapers 20 will be withdrawn by lifting them vertically from the bag 15. However, end panel 31 could also serve as the bottom of the bag during dispensing. In this case, compressed disposable diapers 20 would be withdrawn from the bag 15 with a substantially horizontal motion. In the latter case, the location of the front and back panel extensions could, if desired, be modified so as to overlie end panel 30. In the event the panel extensions are so relocated to overlie end panel 30, care must be exercised when the front and back panel extensions are secured to one another so that the handle thus created does not interfere with removal of the bag material defined by the line of weakness from end panel 30 or with removal of the compressed disposable diapers 20 from the bag 15 after opening of the bag has been effected.

Figure 2:
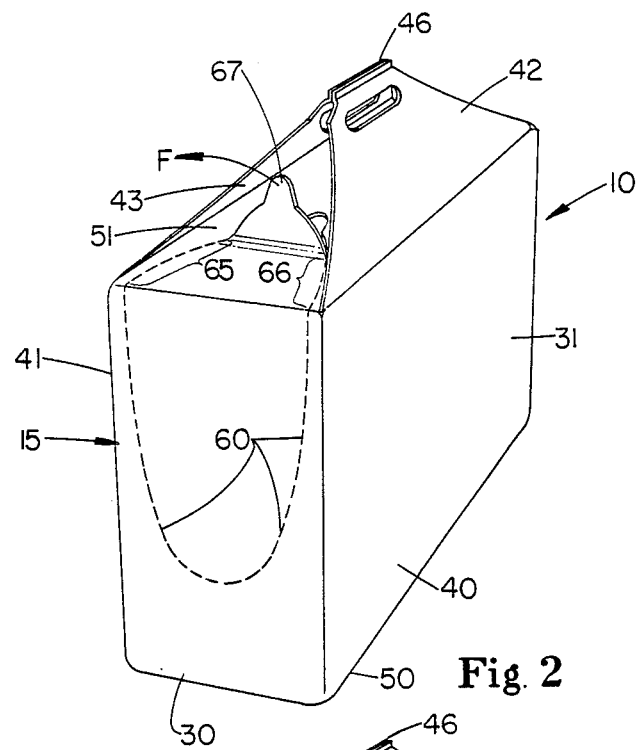
FIG. 2 is a similar simplified perspective view of the bag of FIG. 1, but showing the condition which exists when the tear initiating point is being subjected to a removal force F.

FIG. 2 is a simplified schematic illustration of the easy open flexible bag of compressed flexible articles 10 shown in FIG. 1 once activation of the easy open feature has been initiated. In particular, FIG. 2 illustrates the condition which exists when the tear initiating point 67 in substantially untensioned top panel 51 is subjected to a removal force F, as by gripping tear initiating point 67 between the user's thumb and forefinger and pulling. As can be seen from FIG. 2, lines of perforation 65 and 66 have begun to rupture substantially in parallel with one another. To facilitate smooth propagation of the tears from the substantially untensioned top panel 51 to the tensioned end panel 30 the corners formed between the substantially untensioned top panel 51 and the tensioned end panel 30 may be provided with a greater degree of perforation than either the line of perforations 60 or the lines of perforation 65 and 66 to facilitate easy tearing through the corner portions of the bag where folding gussets are normally present.

Figure 3:
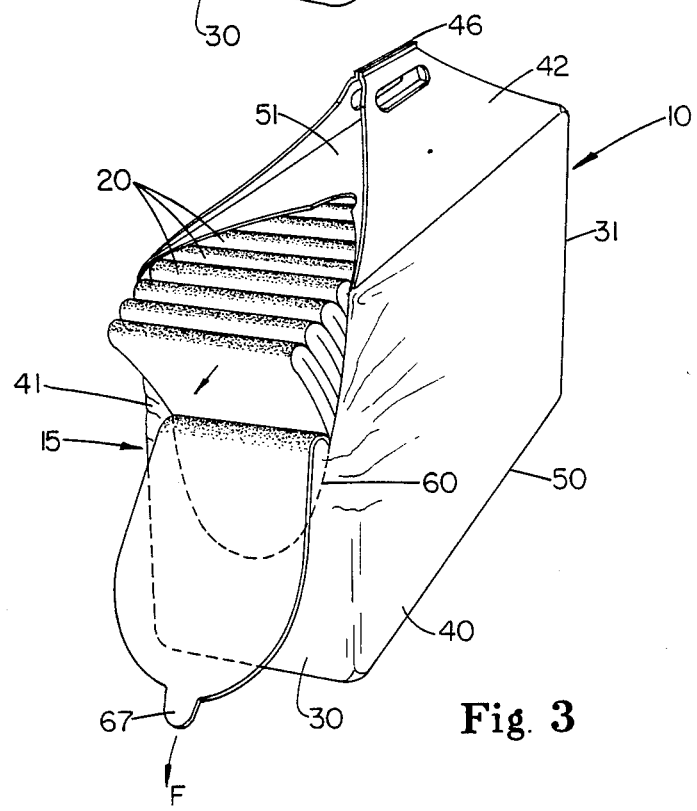
FIG. 3 is a view of the bag shown in FIG. 2 illustrating the condition which exists as tearing along the line of weakness progresses from the substantially untensioned top panel into the tensioned end panel of the bag.

FIG. 3 shows the condition which exists as the tears defined by the continuous line of weakness propagate approximately in parallel from substantially untensioned top panel 51 into tensioned end panel 30 along line of perforations 60 due to the continued influence of an applied grasping force F to tear initiating point 67.

As can best be seen from FIG. 3, the unrestrained folded edges of compressed disposable diapers 20 begin to project through the aperture spanning the substantially untensioned top panel 51 and the tensioned end panel 30 in a fan-like array. This is due to partial release of the compressive forces acting upon the uppermost portion of the stack of compressed disposable diapers contained within the flexible bag 15.

Figure 4:
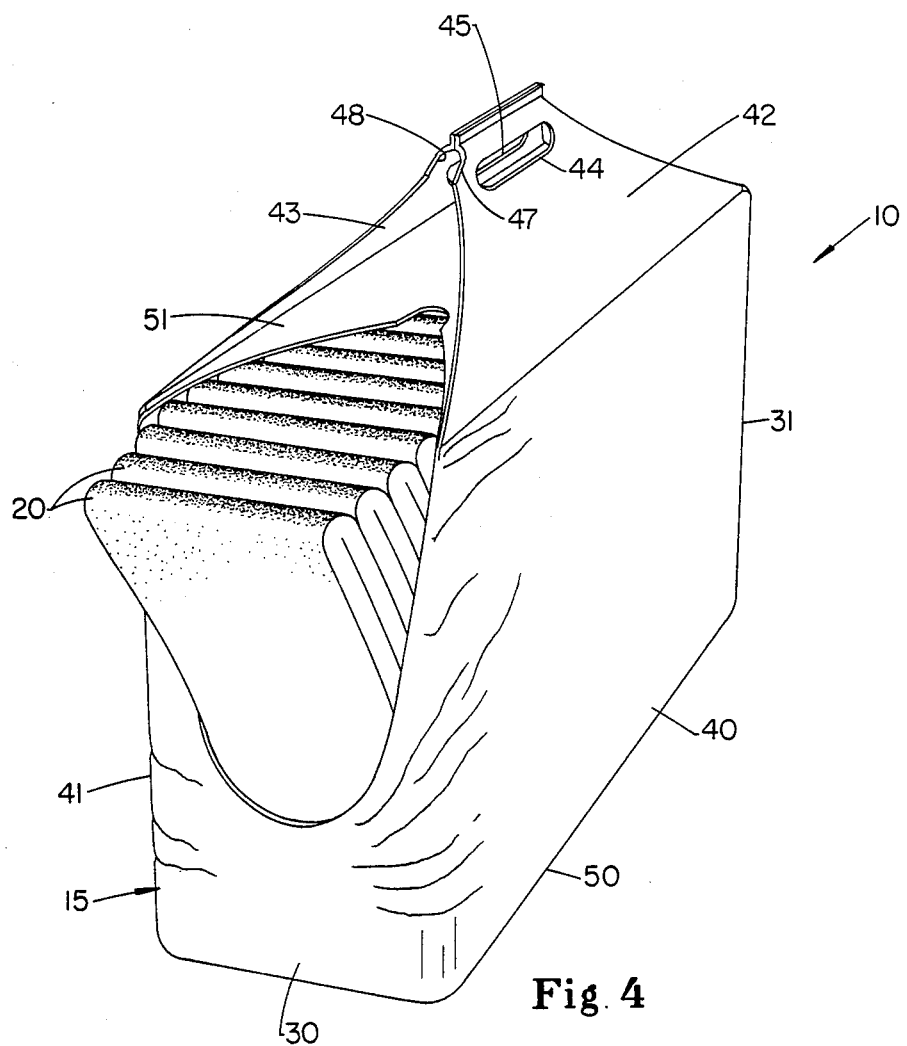
FIG. 4 is a view of the bag shown in FIG. 3 after the material defined by the continuous line of weakness has been completely removed from the bag and the unrestrained portion of the stack of compressed articles has been forced through the aperture thus created by the compressive forces acting upon the articles.

FIG. 4 shows the condition which exists once the entire portion of bag material defined by the continuous line of weakness in substantially untensioned top panel 51 and tensioned end panel 30 has been completely removed from the bag 15. As will be appreciated by those skilled in the art, it is necessary to retain at least a portion of the cross-sectional shape of the folded compressed diapers 20 subject to compression in order to produce the automatic fan-like array illustrated in FIG. 4. While the illustrated embodiment of FIG. 4 depicts removal of about 60% of the depth of tensioned end panel 30, leaving about 40% of the depth of end panel 30 to restrain the stack of compressed flexible articles 20, it has been determined that easy open flexible bags of the present invention can employ apertures spanning up to about 75% of the depth of the tensioned end panel. It has further been observed that in general, it is preferable to provide the portion of the line of weakness 60 contained in tensioned end panel 30 with a shape which converges slightly from its intersection with substantially untensioned top panel 51, where its width is slightly less than that of end panel 30, to its lowermost point. This tends to assist in providing better overall retention of the stack of compressed flexible articles 20 within the bag 15 without impeding the ability of the uppermost portions of the articles 20 to automatically project in a fan-like array through the uppermost portion of the aperture formed in tensioned end panel 30. This restraining action might be likened to the use of a pair of suspenders to hold up the waistband of a pair of trousers on a person having a rotund midsection, i.e., the rotund midsection projects forwardly between the suspenders.

Figure 5:
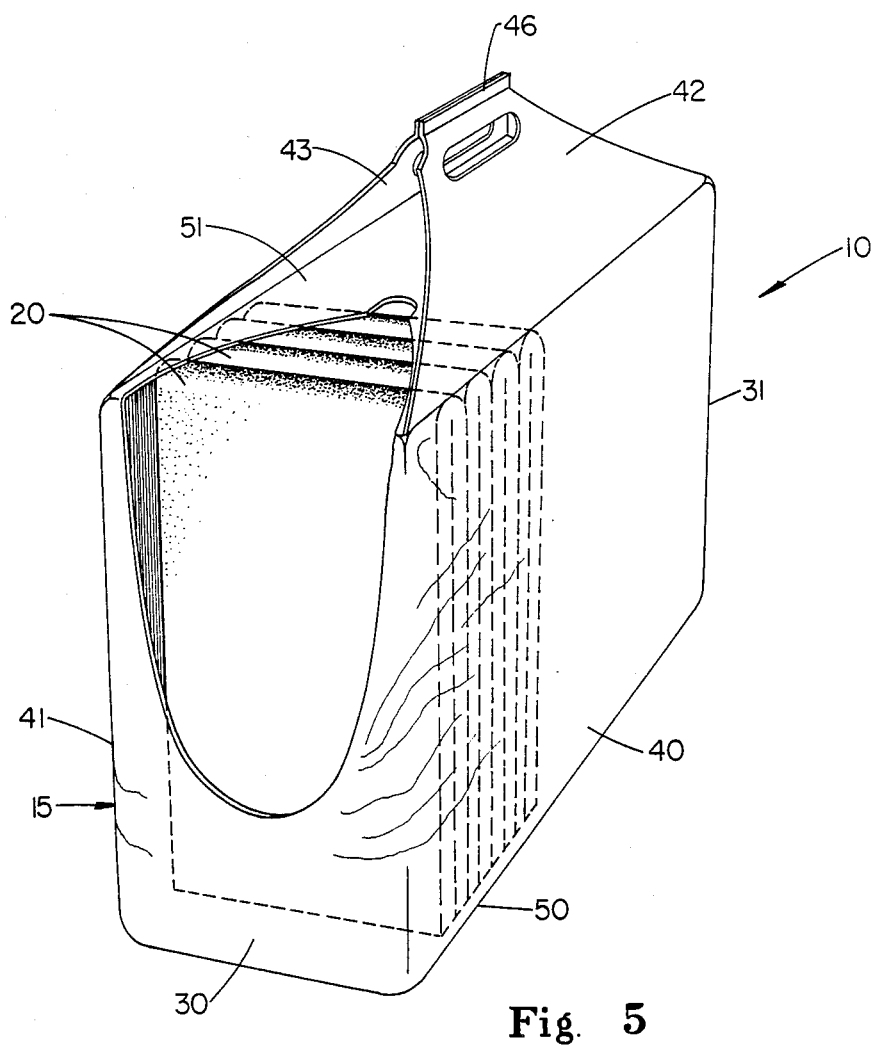
FIG. 5 is a view of the bag shown in FIG. 4 during the latter portions of the dispensing cycle after the compressed articles contained in the bag have returned to their initial substantially uncompressed, thickness.

The tendency of the compressed disposable diapers 20 to project through the aperture formed in the uppermost portion of tensioned end wall 30 of bag 15 will continue throughout a substantial portion of the dispensing cycle of the bag. It will in general be present until such time as the articles remaining within the bag have substantially returned to their substantially uncompressed thickness. However, even when this condition generally illustrated in FIG. 5 has been reached, removal of the remaining articles is still relatively easy for the end user due to the combined exposure provided by the aperture which spans top panel 51 and end panel 30, which by this time is untensioned.

FIGS. 6–11 schematically disclose a particularly preferred method and apparatus for compressing a stack of flexible articles 20 to be housed within an easy open flexible bag 15 of the present invention and for reliably inserting the stack of compressed articles through an open end of a partially pre-erected flexible bag of the present invention.

In particular, FIG. 6 illustrates a stack of disposable diapers 20 prior to compression between a pair of opposing knife belt assemblies. Each knife belt 80,81 rotates about an uppermost roller 82 and a lowermost roller 83. Either the uppermost or lowermost roller must be provided with suitable drive means capable of moving the knife belts 80,81 in the direction shown by the arrows. A smooth surfaced belt support member 84 is preferably located intermediate each pair of rollers 82,83. The opposing ends of each belt support member 84 exhibit an inwardly concave shape approximating that of the adjacent roller to maximize the area of contact between the belt support member 84 and its respective knife belt. Each belt support member 84 is preferably secured in fixed relation to the axis of rotation of the adjacent uppermost roller 82 and the adjacent lowermost roller 83. Each knife belt assembly is laterally moveable in a direction which will compress the stack of flexible disposable diapers 20 located between the knife belts 80,81, as generally shown in FIG. 7. Each knife belt assembly is also vertically moveable so that the knife belts 80,81 containing the stack of compressed disposable diapers 20 can be inserted within the open bottom end of the partially pre-erected flexible bag 15, also as generally shown in FIG. 7.

Figure 8:
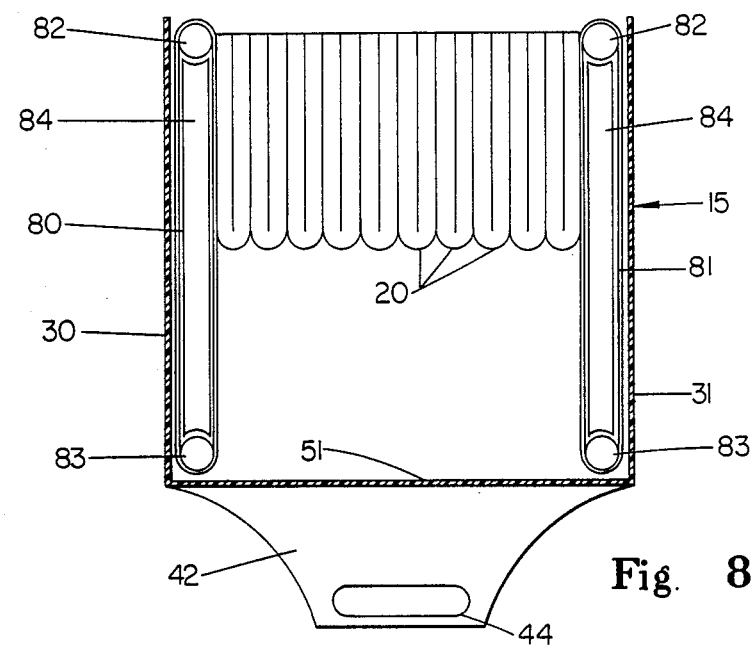
FIG. 8 is a simplified cross-sectional view of the knife belt assemblies and the bag of FIG. 7 after the knife belt assemblies have been inserted within the confines of the partially pre-erected bag.

FIG. 8 illustrates the condition which exists when the knife belt assemblies including knife belts 80,81 have been inserted within the open bottom end of the partially pre-erected flexible bag 15. The amount of compression applied to the flexible disposable diapers 20 is sufficient to allow the compressed stack of disposable diapers and the knife belts 80,81 to pass within the open bottom end of the flexible bag 15 without interference.

Figure 9:
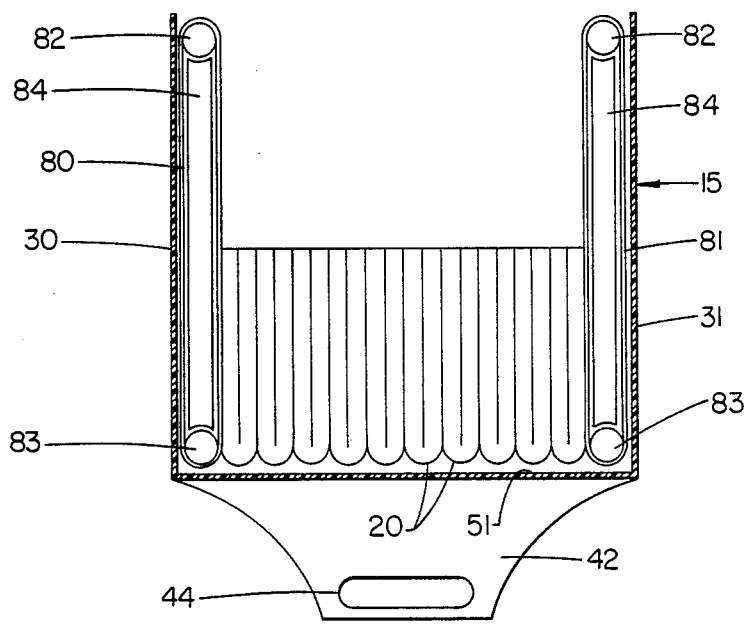
FIG. 9 is a cross-sectional view generally similar to that of FIG. 8, but showing the position of the stack of compressed articles after the knife belts have driven them into contact with the innermost surface of the top panel of the partially pre-erected bag.

Once inside the partially pre-erected flexible bag 15, the drive means for knife belts 80,81 are activated to advance the compressed disposable diapers 20 into final position against the innermost surface of top panel 51 of the partially erected flexible bag 15, as generally shown in FIG. 9. Because the knife belts 80,81 do not contact the innermost surfaces of end panels 30,31 of the flexible bag, no distortion of the flexible bag is caused by activation of the belts.

To withdraw the knife belts assemblies from the open bottom end of the flexible bag 15, the knife belt assemblies are simultaneously extracted without changing their lateral spacing from one another at a first velocity $V_1$. To prevent removal of the compressed disposable diapers 20 from the open bottom end of the bag, the belts 80,81 are driven in the direction shown by the arrows in FIG. 10 at a second velocity $V_2$, which is equal to or slightly greater than the velocity of retraction $V_1$ of the knife belt assemblies. This maintains the compressed disposable diapers 20 in intimate contact with the innermost surface of top panel 51 of the flexible bag 15.

Figure 10:
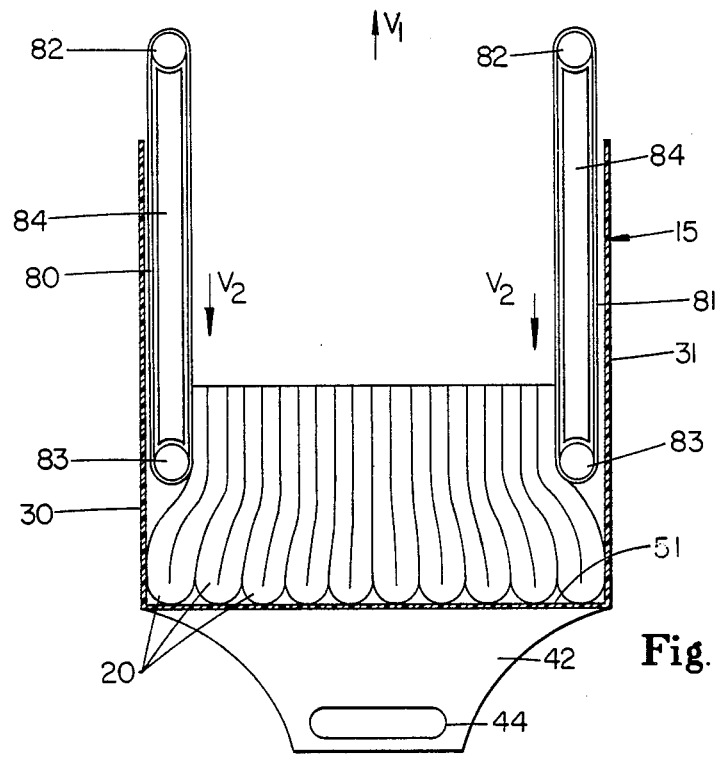
FIG. 10 is a cross-sectional view of the system shown in FIG. 9 as the knife belt assemblies are being retracted from the confines of the bag at a first velocity $V_1$, while the knife belts are operating at a second velocity $V_2$, which is equal to or slightly greater than the velocity of retraction $V_1$.
Figure 11:
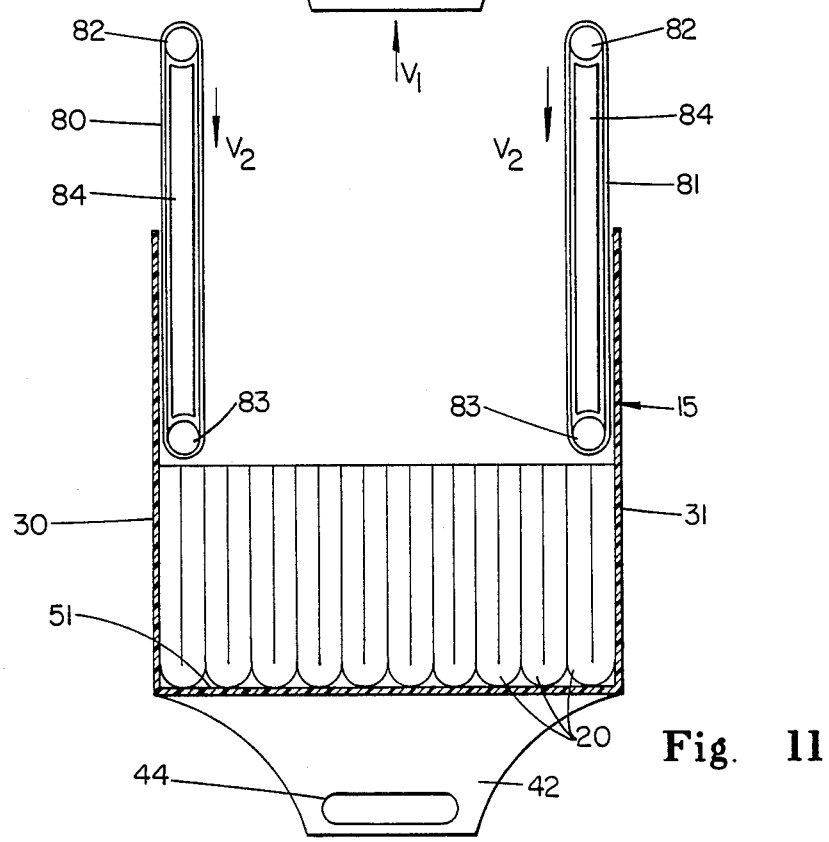
FIG. 11 shows the condition which exists after the knife belts shown in FIG. 10 have completely released control of the stack of compressed flexible articles.

As can also be observed from FIG. 10, the compressed disposable diapers 20 begin to expand immediately as the knife belts 80,81 release control of the stack. This results in the condition generally illustrated in FIG. 11, i.e., the compressed disposable diapers 20 have expanded to occupy the full interior cross-section of the flexible bag 15, thereby relieving, at least to a degree, some of the compression initially imparted to the stack of articles 20 by the knife belts 80,81. As will be appreciated by those skilled in the art, if the amount of compression remaining in the stack of flexible articles within the flexible bag 15 is to be about 50%, then the initial compression which must be imparted by the knife belts 80,81 must be greater than 50%, e.g., perhaps as much as 60% or 70%.

Figure 12:
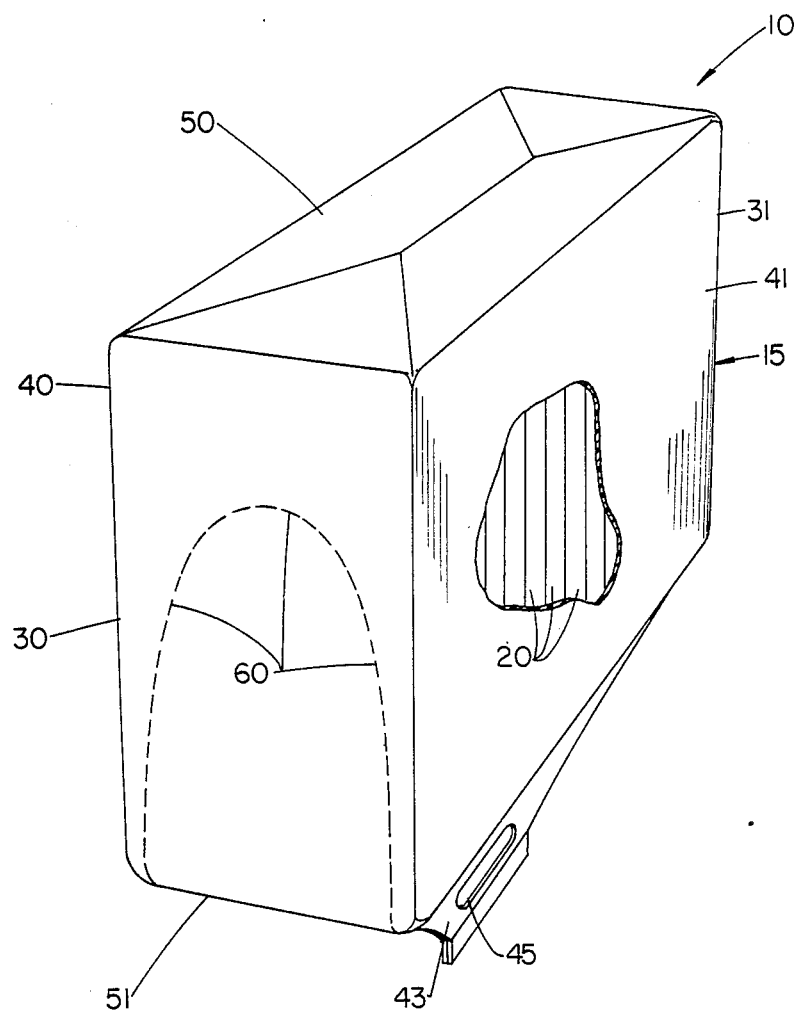
FIG. 12 is a simplified perspective view of the bag shown in cross-section in FIG. 11 after the bottom of the partially pre-erected bag has been folded into gussets and sealed to form a substantially untensioned bottom panel, said view including a broken away segment to more clearly show the content of the bag.

Once the knife belt assemblies have been fully removed from the open bottom end of the flexible bag 15, the open bottom end of the bag is preferably folded in gusset style and the opposing portions of the front and back panels are sealed to one another to form a substantially untensioned bottom panel 50, as generally shown in FIG. 12.

While an easy open flexible bag containing a single stack of compressed flexible articles has been illustrated in the accompanying Drawing Figures, it is recognized that the present invention may be practiced to advantage in bags employing multiple stacks of compressed flexible articles, e.g., one stack superposed upon another stack. In such case, the bag could be provided with a pair of easy opening features of the type disclosed in the illustrated embodiment, one having a tear initiating point in the substantially untensioned top panel, as generally shown in the illustrated embodiment, and the other having a tear initiating point in the substantially untensioned bottom panel (not shown).

As will be appreciated from the foregoing description of a particularly preferred embodiment to the present invention, easy open flexible bags of compressed flexible articles of the present invention have simultaneously reduced the storage, transportation and handling costs typically encountered with flexible articles which are distributed in a substantially uncompressed condition. In addition, they have substantially reduced the cost of the packaging material required by reducing the quantity of packaging material needed to house an identical number of comparable flexible articles in a substantially uncompressed state. Perhaps best of all, however, these significant problems of the prior art packaging systems have been overcome while simultaneously providing substantial benefits to the end user not only in terms of reducing the bulk of the flexible articles prior to actual use, but also in terms of providing highly effective, automatically assisted dispensing of the articles contained within the flexible bag until a substantial portion of the flexible articles have been utilized.

While the present invention has been described in the context of an easy open flexible bag containing flexible compressed disposable diapers, it is recognized that the present invention may also be practiced to advantage in many other applications and environments. Furthermore, the degree of compression to be imparted to the articles can be selected at will by the manufacturer, depending upon the desired end use, the tensile strength of the material selected for the flexible bag and the yield point of the articles. It will be obvious to those skilled in the art that various changes and modifications can be made without departing from the spirit and scope of the present invention, and it is intended to cover in the appended claims all such modifications that are within the scope of this invention.

What is claimed is:

1. An easy open substantially-rectangular flexible bag of compressed flexible articles, said flexible articles being arranged in a stack and held in compression in a direction substantially parallel to their thickness, said bag of articles comprising:
   (a) a front and a back panel connected to one another by means of a pair of end panels, a bottom panel and a top panel, all of said panels being comprised of flexible material;
   (b) a stack of compressed flexible articles oriented so that the substantially planar surface of said articles is aligned substantially parallel to the end panels of said bag and the outermost peripheral edges of the articles contained within said stack are aligned substantially parallel to the front, back, bottom and top panels of said bag, whereby the entire exposed substantially planar surface of the outermost article at each end of said stack intimately contacts the innermost surface of the adjacent end panel, while only the outermost peripheral edges of said articles contained within said stack contact said front, back, top and bottom panels, said end panels and at least one pair of said front and back or said top and bottom panels being subject to tension imposed by said stack of compressed flexible articles, the other pair of said front and back or said top and bottom panels being in a substantially untensioned condition; and
   (c) an easy open device comprising a substantially continuous line of weakness located partially within one of said tensioned end panels and partially within the adjacent untensioned panel, said substantially continuous line of weakness defining a predetermined portion of said end panel to be separated from the remainder of said end panel without releasing the tension in the remainder of said end panel and an unobstructed removable tear initiating point in said substantially untensioned panel, said predetermined portion of said end panel having an area substantially coinciding with up to about 75 percent of the cross-sectional area of the articles of said stack, whereby said predetermined portion of said end panel is separated from the remainder of said end panel by applying a grasping force to said tear initiating point in said substantially untensioned panel and propagating tears in the portion of said line of weakness which extends into said substantially untensioned panel and thereafter causing said tears to propagate into said adjacent end panel along said line of weakness whereupon the portion of the stack of articles coinciding with the aperture thus formed in said end panels expands through said aperture in a fan-like array while the portion of said stack coinciding with the remaining tensioned portion of said end panel is retained in a substantially compressed condition.

2. The flexible bag of compressed flexible articles of claim 1, wherein at least one supporting loop is provided over said substantially untensioned panel containing said portion of said line of weakness, said loop serving as a means of carrying said bag.

3. The flexible bag of compressed flexible articles of claim 2, wherein said front and back panels are in a tensioned condition and wherein said loop includes a pair of apertures sized to accommodate the user's fingers in a pair of panels vertically extending from the tensioned front and back panels of said bag, said extended panels being secured to one another in an area located vertically above said apertures.

4. The flexible bag of compressed flexible articles of claim 3, wherein said extended panels exhibit a generally tapered shape from the end panels of said bag to their area of securement to one another.

5. The flexible bag of compressed flexible articles of claim 4, wherein the portion of said line of weakness in said substantially untensioned panel of said bag generally coincides with the tapered edges of said extended panels containing said apertures when said bag is viewed from directly overhead.

6. The flexible bag of compressed flexible articles of claim 5, wherein said portion of said line of weakness in said substantially untensioned panel is generally triangular and wherein the tip of said triangle includes a readily accessible grasping tab comprising said tear initiating point for initiating said tear.

7. The flexible bag of compressed flexible articles of claim 6, said bag further including graphical indicia to direct the user's attention to said grasping tab comprising said tear initiating point.

8. The flexible bag of compressed flexible articles of claim 7, wherein said graphical indicia on said bag are on said substantially untensioned panel containing said portion of said line of weakness.

9. The flexible bag of compressed flexible articles of claim 7, wherein said graphical indicia are on said extended tapered panels containing said apertures sized to accommodate the user's fingers.

10. The flexible bag of compressed flexible articles of claim 1, wherein the material comprising said flexible bag is selected from the group consisting of polymeric films, papers, nonwovens and laminate structures comprised of two or more of the aforementioned materials.

11. The flexible bag of compressed flexible articles of claim 10, wherein said line of weakness is comprised of perforations in the material comprising said flexible bag.

12. The flexible bag of compressed flexible articles of claim 11, wherein the perforations in said substantially untensioned panel are less resistant to applied tearing forces than the perforations in said tensioned end panel.

* * * * *

UNITED STATES PATENT AND TRADEMARK OFFICE
CERTIFICATE OF CORRECTION

PATENT NO. : 4,934,535

DATED : June 19, 1990

INVENTOR(S) : Delmar R. Muckenfuhs and James C. Baird

It is certified that error appears in the above-identified patent and that said Letters Patent is hereby corrected as shown below:

Title page, "Cincinatti" should read -- Cincinnati --.

In the Abstract, line 10, after "articles" insert -- and --.

Signed and Sealed this

Seventh Day of July, 1992

Attest:

DOUGLAS B. COMER

*Attesting Officer*  *Acting Commissioner of Patents and Trademarks*